US010369026B2

(12) United States Patent
Toler

(10) Patent No.: US 10,369,026 B2
(45) Date of Patent: Aug. 6, 2019

(54) CLAMPING QUICK CONNECT MECHANISM FOR AXIAL ATTACHMENT

(71) Applicant: Zimmer, Inc., Warsaw, IN (US)

(72) Inventor: Jason S. Toler, Pierceton, IN (US)

(73) Assignee: Zimmer, Inc., Warsaw, IN (US)

( * ) Notice: Subject to any disclaimer, the term of this patent is extended or adjusted under 35 U.S.C. 154(b) by 97 days.

(21) Appl. No.: 15/647,605

(22) Filed: Jul. 12, 2017

(65) Prior Publication Data

US 2018/0014951 A1 Jan. 18, 2018

Related U.S. Application Data

(60) Provisional application No. 62/362,667, filed on Jul. 15, 2016.

(51) Int. Cl.

*A61F 2/60* (2006.01)
*A61F 2/76* (2006.01)
*A61F 2/78* (2006.01)
*A61F 2/80* (2006.01)
*F16B 2/00* (2006.01)
*F16B 2/02* (2006.01)
*F16B 2/18* (2006.01)
*F16B 7/04* (2006.01)
*F16B 7/14* (2006.01)

(52) U.S. Cl.

CPC .................. *A61F 2/76* (2013.01); *A61F 2/60* (2013.01); *A61F 2/80* (2013.01); *F16B 2/02* (2013.01); *A61F 2002/7887* (2013.01); *F16B 2/00* (2013.01); *F16B 2/185* (2013.01); *F16B 7/0426* (2013.01); *F16B 7/1454* (2013.01)

(58) Field of Classification Search

CPC ...... A61F 2/60; A61F 2/76; A61F 2/78; A61F 2/80; A61F 2002/7887; A61F 2002/6854; A61F 2002/5083; Y10T 403/7071; Y10T 403/04; F16B 2/00; F16B 2/02; F16B 2/0426; F16B 2/1454; F16B 2/185; F16B 3/00

See application file for complete search history.

(56) References Cited

U.S. PATENT DOCUMENTS 2,696,649 A * 12/1954 Clapper .................. E04G 25/04 403/344
4,573,717 A * 3/1986 Peacock .................. F16B 2/185 24/270
4,705,305 A * 11/1987 Ghaly ....................... F16B 2/08 24/270
5,479,836 A * 1/1996 Chang .................... B62H 5/001 70/201
2002/0149123 A1* 10/2002 Edel ...................... B01F 3/0412 261/122.1
2005/0049720 A1* 3/2005 Benson ..................... A61F 2/76 623/38
2008/0288087 A1* 11/2008 Bachus ................. A61F 2/2814 623/34
2015/0164659 A1* 6/2015 Konishi .................... A61F 2/76 623/27

* cited by examiner

*Primary Examiner* — Christie L Bahena

(74) *Attorney, Agent, or Firm* — Schwegman Lundberg & Woessner, P.A.

(57) ABSTRACT

An apparatus including a post connectable to an implant extending from a residual limb; a base connectable to a prosthesis; and a clamping assembly configured to releasably connect the post to the base.

8 Claims, 3 Drawing Sheets

116 112 114 122 118 120 132 133 138 135 136 134 110 106 100 108 104 130 103 102

CLAMPING QUICK CONNECT MECHANISM FOR AXIAL ATTACHMENT

CLAIM OF PRIORITY

This application claims the benefit of U.S. Provisional Patent Application Ser. No. 62/362,667, filed on Jul. 15, 2016, the benefit of priority of which is claimed hereby, and which is incorporated by reference herein in its entirety.

FIELD

The present subject matter relates to an apparatus for use with a prosthesis and more specifically for mechanism for use in attaching a prosthesis to a limb.

BACKGROUND

It is common to attach a prosthesis or artificial limb externally onto a residual limb of an individual which has been amputated or otherwise severed in order to provide a measure of use of the limb to the individual. It can be time-consuming to attach the prosthesis and a robust, slop-free connection can be difficult to achieve.

OVERVIEW

In a first example, an apparatus includes a post connectable to an implant extending from a residual limb; a base connectable to a prosthesis; and a clamping assembly configured to releasably connect the post to the base.

In example 2, the post of example 1 can include a proximal end having a female taper to receive a male taper of the implant.

In example 3, the post of example 1 can include a distal end and the base can include an internal cavity to receive the distal end of the post.

In example 4, the clamping assembly of example 1 can include a clamp ring connected to the base, the clamp ring configured to receive the post within the clamp ring.

In example 5, the clamping assembly of example 4 can further include a lever configured to move the clamp ring between an open state and a closed state, wherein in the open state the post can freely move within the clamp ring, and in the closed state the post is coupled to the base via the clamp ring.

In example 6, the apparatus of example 4 can include an outer surface of the post including a chamfered surface and the clamp ring including an opposing inner chamfered surface such that when the clamp ring is moved to a closed state the inner chamfered surface of the clamp ring applies a force against the chamfered outer surface of the post to drive a distal end surface of the post against a surface within a cavity of the base.

In example 7, the clamping assembly of example 1 can further include a clamp ring coupled to the base around an upper opening of a cavity in the base, the clamp ring including an open ring portion and a pair of arms extending from the open ring portion, the clamping assembly further including a rod extending through holes located in each of the pair of arms, a bearing located at an outer portion of one of the pair of arms with the rod also extending through the bearing, the clamping assembly further including a lever rotatably coupled to an end of the rod, the lever including a cam portion to move against the bearing, wherein activating the lever moves the clamp ring between an open state and a closed state.

In example 8, the clamp ring of example 7 can be coupled within a groove located on an inner surface of the base around the cavity.

In example 9, the apparatus of example 1 can include a distal end of the post includes a keyed portion to cooperate with an opposed keyed portion within a cavity of the base.

In example 10, an apparatus can include a post connectable to an implant extending from a residual limb; a base connectable to a prosthesis, the base including a cavity to removably receive the post; and a clamping assembly configured to releasably connect the post to the base; wherein the clamping assembly is configured such that closing the clamping assembly around the post drives a distal end surface of the post against a surface within the cavity of the base.

In example 11, the apparatus of example 10 can include an outer surface of the post including a chamfered surface and a portion of the clamping assembly including an opposing inner chamfered surface such that when the clamping assembly is closed, the inner chamfered surface of the clamping assembly applies a force against the chamfered outer surface of the post to drive the distal end surface of the post against the surface within the cavity of the base.

In example 12, the apparatus of example 11 can include the portion of the clamping assembly having the opposed inner chamfered surface including a clamp ring coupled to the base, the clamp ring configured to receive the post.

In example 13, the clamping assembly of example 12 can further include a lever configured to move the clamp ring between an open state and a closed state, wherein in the open state the post can freely move within the clamp ring, and in the closed state the post is coupled to the base via the clamp ring.

In example 14, the clamp ring of example 13 can be coupled to the base around an upper opening of a cavity in the base, the clamp ring including an open ring portion and a pair of arms extending from the open ring portion, the clamping assembly further including a rod through holes in the pair of arms, a bearing located at an outer portion of one of the pair of arms with the rod also extending through the bearing, the clamping assembly further including a lever rotatably coupled to an end of the rod, the lever including a cam portion to engage with the bearing, wherein activating the lever moves the clamp ring between the open state and the closed state.

In example 15, the post of example 14 can include a proximal end having a female taper to receive a male taper of the implant.

In example 16 a method includes providing a post configured to be connectable to an implant extending from a residual limb; providing a base configured to be connectable to a prosthesis, the base including a cavity to removably receive the post; and releasably connecting the post to the base using a clamping assembly; wherein the clamping assembly is configured such that closing the clamping assembly around the post drives a distal end surface of the post against a surface within the cavity of the base.

In example 17, the method of example 16 can include an outer surface of the post including a chamfered surface and a portion of the clamping assembly including an opposing inner chamfered surface such that when the clamping assembly is closed, the inner chamfered surface of the clamping assembly applies a force against the chamfered outer surface of the post to drive the distal end surface of the post against the surface within the cavity of the base.

In example 18, the method of example 17 can include the portion of the clamping assembly having the opposed inner chamfered surface including a clamp ring coupled to the, the clamp ring configured to receive the post.

In example 19, the clamping assembly of example 18 can further include a lever configured to move the clamp ring between an open state and a closed state, wherein in the open state the post can freely move within the clamp ring, and in the closed state the post is coupled to the base via the clamp ring.

In example 20, the clamp ring of example 19 can be coupled to the base around an upper opening of a cavity in the base, the clamp ring including an open ring portion and a pair of arms extending from the open ring portion, the clamping assembly further including a rod through holes in the pair of arms, a bearing located at an outer portion of one of the pair of arms with the rod also extending through the bearing, the clamping assembly further including a lever rotatably coupled to an end of the rod, the lever including a cam portion to engage with the bearing, wherein activating the lever moves the clamp ring between the open state and the closed state.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
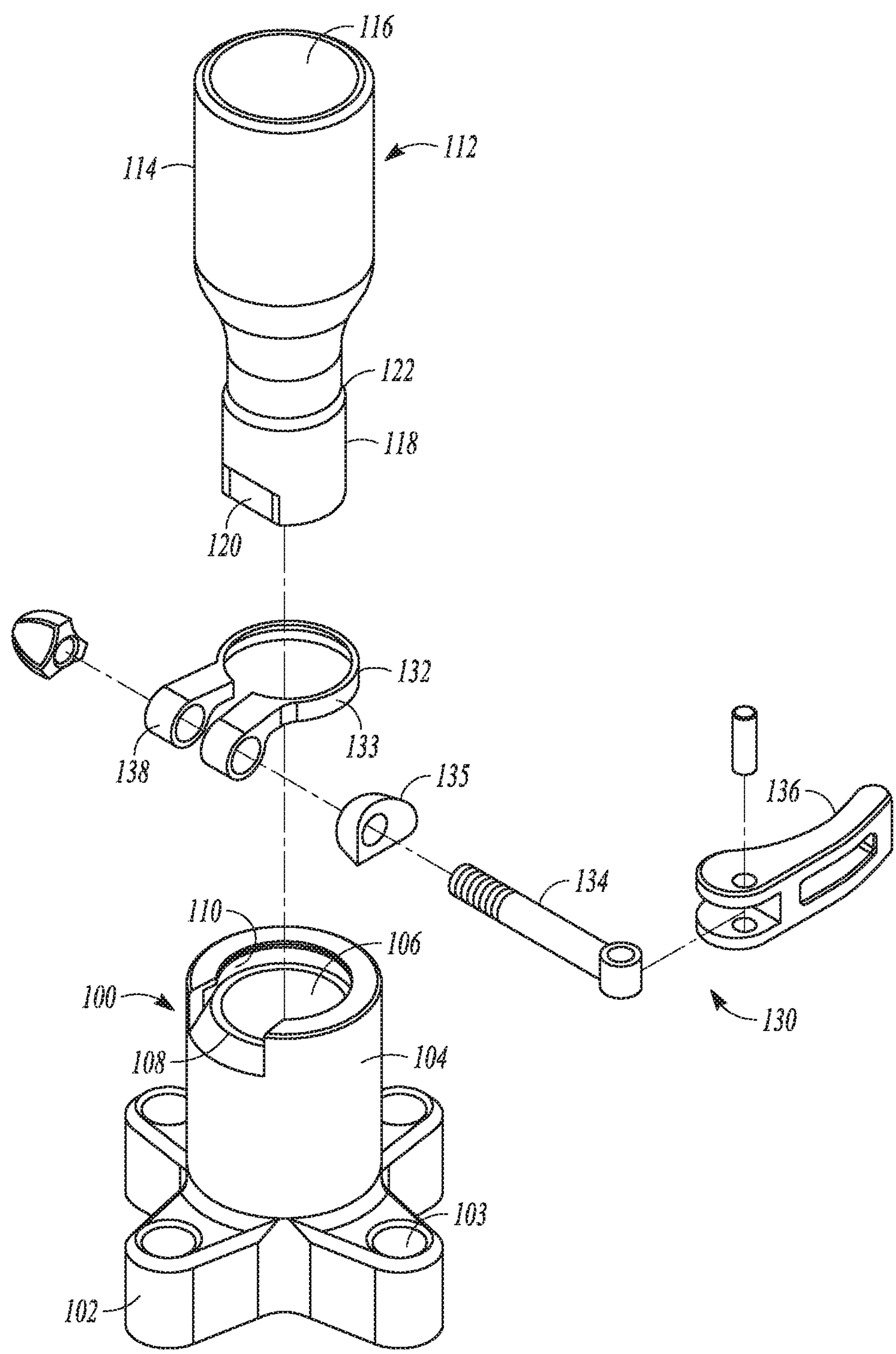
FIG. 1 shows an exploded perspective view of a connect mechanism in accordance with one embodiment.
Figure 2:
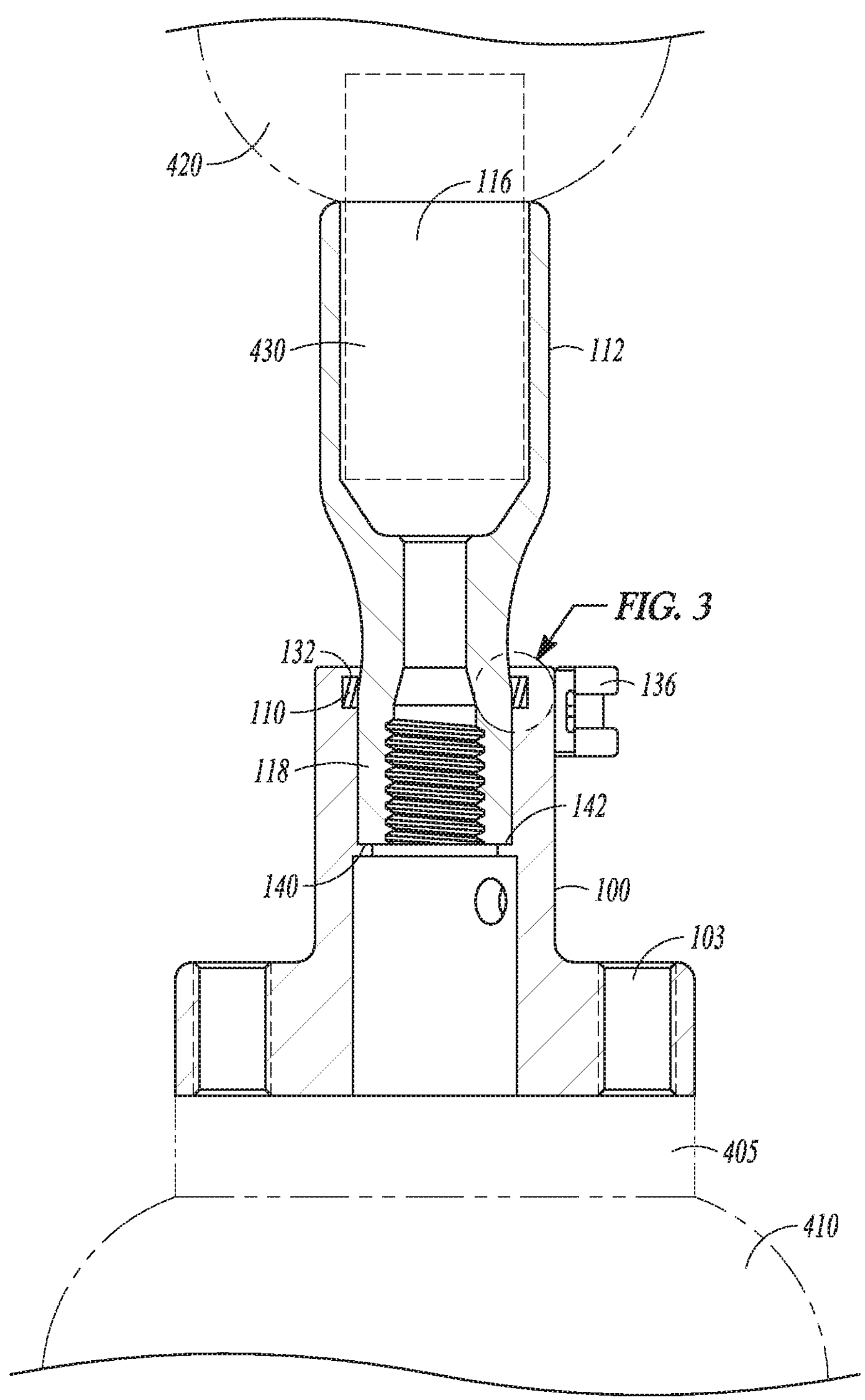
FIG. 2 shows a cross-section side view of the connect mechanism of FIG. 1, in accordance with one embodiment.

FIG. 1 shows an exploded perspective view of a connect mechanism for attaching a prosthesis to a residual limb of an amputated leg, in accordance with one embodiment. FIG. 2 shows a cross-section side view of the connect mechanism with the connect mechanism being attached to a schematically shown residual limb 420 and a prosthesis 410.

In one example, the connect mechanism can generally include a post 112 connectable to a transdermal implant 430 extending from the residual limb 420, and a base 100, which can be a part of a fail-safe mechanism along with an attachment plate 405, and which can be directly or indirectly connectable to the prosthesis 410. The connect mechanism further includes a clamping assembly 130 configured to releasably connect the post 112 to the base 100. The clamping assembly 130 allows the prosthesis 410 to be easily and quickly removed from and re-attached to the residual limb 420. In an example, the base 100 and the plate 405 of the fail-safe mechanism can be connected via a spring component that can flex. When a large enough bending moment is applied, the spring flexes enough to allow the base 100 and the plate 405 plates to separate.

The post 112 can include a proximal end 114 having an internal female taper 116 to receive a corresponding male taper of the implant 430. The implant 430 is implanted into the residual limb 420. The post 112 can further include a distal end 118 and the base 100 can include an internal cavity 106 to receive the distal end 118 of the post 112. In one example, the distal end 118 of the post 112 includes a keyed portion 120 to cooperate with an opposed keyed portion (not shown) within the internal cavity 106 within an upper portion 104 of the base 100. The post 112 can also include internal threads on the distal end 118 of the post. The threads can be used to remove the post 112 from the implant 430 using an axial taper separator. For example, the taper separator can have an internal plunger that will fit through the smaller clearance hole in the post 112 to apply pressure to the tapered implant 430.

The clamping assembly 130 can include a clamp ring 132 coupled to the base 100. The clamp ring 132 can be configured to receive the post 112 when the post 112 is inserted into the internal cavity 106. In one example, the clamping assembly 130 includes the clamp ring 132 coupled to the base 100 around an upper opening of the internal cavity 106 in the base 100. For example, a groove 110 can be formed on an inner surface around the upper opening of the internal cavity 106 and the clamp ring 132 can be held within the groove 110.

The clamp ring 132 can include an open ring portion 133 and a pair of arms 138 extending from the open ring portion 133. The base 100 can include a notch 108 in the upper portion 104 to accommodate the arms 138 such that the ends of the arms 138 extend outside the upper portion 104 of the base 100. The clamping assembly 130 can further include a rod 134 extending through holes located in each of the pair of arms 138 and a bearing 135 located at an outer portion of one of the pair of arms 138 with the rod 134 also extending through the bearing 135.

The clamping assembly 130 can include a lever 136 configured to move the clamp ring 132 between an open state and a closed state. For example, in the open state the post 112 can freely move back and forth within the clamp ring 132, and in the closed state the post 112 is coupled to the base 100 via the clamp ring 132.

In one example, the lever 136 can be rotatably coupled to an end of the rod 134 and the other end of the rod 134 is coupled by a nut to the other side of arms 138. The lever 136 can include a cam portion to move against the bearing 135. When the lever 136 is rotated in one direction, the cam portion is configured to pull the rod 134 so as to exert pressure to squeeze the arms 138 together. When the lever 136 is rotated in the opposite direction, the cam portion pushes the rod 134 away which allows the arms 138 to open. Thus, activating the lever 136 moves the clamp ring 132 between the open state and the closed state.

Figure 3:
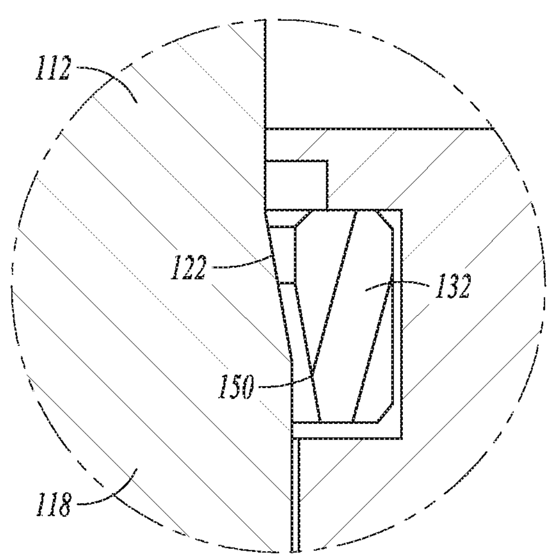
FIG. 3 shows a close-up of a portion of FIG. 2, in accordance with one embodiment.

Referring now also to FIG. 3, which shows a close-up of a portion of FIG. 2, an outer surface of the post 112 towards the distal end 118 can include a chamfered surface 122 and the clamp ring 132 includes an opposing inner chamfered surface 150. In one example, when the clamp ring 132 is moved to the closed state by closing the lever 136, the inner chamfered surface 150 of the clamp ring 132 applies a downward force against the chamfered outer surface 122 of the post 112 to drive a distal end surface 140 of the post 112 against an opposing surface 142 within the internal cavity 106 of the base 100.

Thus, the clamping assembly 130 can be configured such that closing the clamping assembly 130 around the post 112 drives the distal end surface 140 of the post 112 against the opposing surface 142 within the cavity 106 of the base 100. By driving the post 112 tightly against the opposing surface of the post 100, the clamping assembly 130 holds the connecting mechanism tightly together and accordingly, the prostheses 410 is tightly held the residual limb 420. Specifically, during a downward stride of the user on the prosthesis 410, the upward force is directly transferred through the prosthesis to base 100 and then directly to post 112 and then the implant 430. Likewise, when the prosthesis 410 is raised, there is no slop in the connection because the post 112 is tightly held to the base 100.

Accordingly, when loaded axially (e.g. when a patient walks on the prosthesis), the load is transferred directly from the base 100 to the implant 430 via the connecting surfaces 140, 142 when the post 112 is within the cavity 106. Thus, the load is not applied directly to the clamping assembly 130. Thus, the clamping assembly 130 can support the weight of the prosthesis in tension, which is much less than the compressive load requirements of the implant construct.

In an example use, a surgeon implants the tapered implant 430 into a patient's femur after a transfemoral amputation, for example. The post 112 is attached to the implant 430 with a tapered connection. The base 100 can be part of the overall fail-safe mechanism along with plate 405 and can be directly or indirectly connected to an appropriate prosthesis 410, for example.

When the patient wants to put on the prosthesis 410, the lever 136 is moved so that the clamp ring 132 is in the open state, and the distal end 118 of the post 112 is inserted through the clamp ring 132 and into the cavity 106 of the base 100. The lever 136 is then rotated so as to pull the rod 134 and squeeze arms 138 together, thus tightening the clamp ring 132 around the post 112. Also, the chamfered surface 150 of the clamp ring 132 applies downward force against the opposing chamfered surface 122 of the post 112 so as to drive the post 112 down into the cavity 106 so that the post 112 bottoms out within the cavity 106 on the surface 142 of the base 100.

To remove the prosthesis the user simply reverse the steps and rotates the lever 136 to cause the clamp ring 132 to move to the open state and the post 112 is slipped out of the cavity 106. Thus, the present connection assembly provides a quick on/off, yet stable and robust connection with reduced slop while still allowing the load to be transferred directly from the base 100 to the implant 430 through the interface of the post 112 and the base 100 without requiring the clamping assembly 130 to bear the load.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus comprising: a post connectable to an implant extending from a residual limb; a base connectable to a prosthesis; and a clamping assembly configured to releasably connect the post to the base; wherein the post includes a distal end and the base includes an internal cavity to receive the distal end of the post; wherein the clamping assembly includes a clamp ring coupled to the base around an upper opening within the internal cavity of the base, the clamp ring including an open ring portion and a pair of arms extending from the open ring portion, the clamping assembly further including a rod extending through holes, wherein in each of the arms includes one of the holes, a bearing located at an outer portion of one of the arms with the rod also extending through the bearing, the clamping assembly further including a lever rotatably coupled to an end of the rod, the lever including a cam portion to move against the bearing, wherein activating the lever moves the clamp ring between an open state and a closed state; wherein the distal end of the post includes a keyed portion to cooperate with an opposed keyed portion within the internal cavity of the base and the pair of arms extends through the keyed portion of the base.

2. The apparatus of claim 1, wherein the post includes a proximal end having a female portion that is tapered to receive a male portion that is tapered of the implant.

3. The apparatus of claim 1, wherein the clamp ring is configured to receive the post within the clamp ring.

4. The apparatus of claim 3, wherein in the open state the post can freely move within the clamp ring, and in the closed state the post is coupled to the base via the clamp ring.

5. The apparatus of claim 3, wherein an outer surface of the post includes a chamfered surface and the clamp ring includes an opposing inner chamfered surface such that when the clamp ring is moved to a closed state the inner chamfered surface of the clamp ring applies a force against the chamfered outer surface of the post to drive a distal end surface of the distal end of the post against a surface within the cavity of the base.

6. The apparatus of claim 1, wherein the clamp ring is coupled within a groove located on an inner surface of the base around the cavity.

7. An apparatus comprising: a post connectable to an implant extending from a residual limb; a base connectable to a prosthesis, the base including a cavity to removably receive the post; and a clamping assembly configured to releasably connect the post to the base; wherein the clamping assembly is configured such that closing the clamping assembly around the post drives a distal end surface of the post against a surface within the internal cavity of the base; wherein an outer surface of the post includes a chamfered surface and a portion of the clamping assembly includes an opposing inner chamfered surface such that when the clamping assembly is closed, the inner chamfered surface of the clamping assembly applies a force against the chamfered outer surface of the post to drive the distal end surface of the post against the surface within the internal cavity of the base; wherein the portion of the clamping assembly having the opposed inner chamfered surface includes a clamp ring coupled to the base, the clamp ring configured to receive the post; wherein the clamping assembly further includes a lever configured to move the clamp ring between an open state and a closed state, wherein in the open state the post can freely move within the clamp ring, and in the closed state the post is coupled to the base via the clamp ring; wherein the clamp ring is coupled to the base around an upper opening of the internal cavity within the base, the clamp ring including an open ring portion and a pair of arms extending from the open ring portion, the clamping assembly further including a rod extending through a hole in each of the arms, a bearing located at an outer portion of one of the pair of arms with the rod also extending through the bearing, the clamping assembly further including a lever rotatably coupled to an end of the rod, the lever including a cam portion to engage with the bearing, wherein activating the lever moves the clamp ring between the open state and the closed state; wherein the distal end of the post includes a keyed portion to cooperate with an opposed keyed portion within the internal cavity of the base and the pair of arms extends through the keyed portion of the base.

8. The apparatus of claim 7, wherein the post includes a proximal end having a female portion that is tapered to receive a male portion that is tapered of the implant.

* * * * *

UNITED STATES PATENT AND TRADEMARK OFFICE

CERTIFICATE OF CORRECTION

PATENT NO. : 10,369,026 B2
APPLICATION NO. : 15/647605
DATED : August 6, 2019
INVENTOR(S) : Jason S. Toler It is certified that error appears in the above-identified patent and that said Letters Patent is hereby corrected as shown below:

In the Claims

In Column 6, Line 27, in Claim 1, after “comprising:”, insert --¶--

In Column 6, Line 28, in Claim 1, after “limb;”, insert --¶--

In Column 6, Line 29, in Claim 1, after “and”, insert --¶--

In Column 6, Line 30, in Claim 1, after “base;”, insert --¶--

In Column 6, Line 32, in Claim 1, after “post;”, insert --¶--

In Column 6, Line 44, in Claim 1, after “state;”, insert --¶--

In Column 7, Line 1, in Claim 7, after “comprising:”, insert --¶--

In Column 7, Line 2, in Claim 7, after “limb;”, insert --¶--

In Column 7, Line 4, in Claim 7, after “and”, insert --¶--

In Column 7, Line 5, in Claim 7, after “base;”, insert --¶--

In Column 7, Line 19, in Claim 7, after “post;”, insert --¶--

In Column 8, Line 2, in Claim 7, after “ring;”, insert --¶--

Signed and Sealed this
Seventh Day of April, 2020

Andrei Iancu
*Director of the United States Patent and Trademark Office*